United States Patent [19]

Kozuka et al.

[11] Patent Number: 4,869,094
[45] Date of Patent: Sep. 26, 1989

[54] GAS SAMPLING VALVE

[75] Inventors: Kazuhiro Kozuka; Toshihiro Ozasa; Hideaki Takahashi; Haruyoshi Kondo, all of Aichi, Japan

[73] Assignee: Kabushiki Kaisha Toyota Chuo Kenkyusho, Aichi, Japan

[21] Appl. No.: 214,548

[22] Filed: Jul. 1, 1988

[30] Foreign Application Priority Data

Jul. 2, 1987 [JP] Japan ................. 62-165629

[51] Int. Cl.$^4$ ......................................... G01M 15/00
[52] U.S. Cl. ........................................ 73/2.6; 73/864.81
[58] Field of Search ................... 73/118.1, 864.81, 26, 73/864.21; 123/489; 204/424

[56] References Cited

U.S. PATENT DOCUMENTS

| 3,807,233 | 4/1974 | Crawford | 73/864.81 X |
|---|---|---|---|
| 4,117,815 | 10/1978 | Ikeura | 123/489 |
| 4,177,787 | 12/1979 | Hattori et al. | 123/489 |
| 4,663,017 | 5/1987 | Ross | 204/424 X |
| 4,752,361 | 6/1988 | Gautschi | 204/424 X |

FOREIGN PATENT DOCUMENTS 3224347 8/1983 Fed. Rep. of Germany ...... 123/489

OTHER PUBLICATIONS

Haaland, D. M., Noncatalytic Electrodes ... Oxygen Sensors, J. Electrochem. Soc., vol. 127, No. 4, Apr. '80, pp. 796–804.
Badwal, S. et al, Low-Temperature ... Oxygen Sensors, for Advances in Ceramics, vol. 12, 1984, pp. 598–606.
Society of Automotive Engineers, Inc., "Diesel Combustion Chamber Sampling—Hardware, Procedures, and Data Interpretation"—James E. Bennethum, et al.
"Development of the Toyota Lean Combustion System"-Souich Matsushita et al.

Primary Examiner—Jerry W. Myracle
Attorney, Agent, or Firm—Oblon, Spivak, McClelland, Maier & Neustadt

[57] ABSTRACT

A gas sampling valve is provided with a small opening for gas sampling and a gas flow channel communicating therewith and is adapted to sample a gas in the gas flow passage by operating a valve for opening and closing the small opening, wherein at least one detector for detecting the concentration of oxygen or combustion gas is disposed in the gas flow passage, whereby the concentration of oxygen, an air excess ratio, the combustion efficiency, or the like can be measured without using a separate analyzer.

14 Claims, 14 Drawing Sheets

FIG. 2

(1) [S]-[A]→
- $O_2$ CONCENTRATION IN SAMPLED GAS
  (LEAN SIDE RELATIVE TO THEORETICAL AIR FUEL RATIO)

(2) [S]-[Cat.]-[A]→ $O_2$ CONCENTRATION MEASUREMENT AFTER COMBUSTION USING CATALYZER
$CO+O_2 \rightarrow CO_2$
$HC+O_2 \rightarrow CO_2+H_2O$
- AIR FUEL RATIO (LEAN SIDE RELATIVE TO THEORETICAL AIR FUEL RATIO)

(3) [S]-[B]→ CATALYTIC ACTION ON SENSOR SURFACE $O_2$ CONC. MEASUREMENT ON SENSOR SURFACE
$CO+O_2 \rightarrow CO_2$
$HC+O_2 \rightarrow CO_2+H_2O$
- AIR FUEL RATIO (LEAN SIDE RELATIVE TO THEORETICAL AIR FUEL RATIO)

(4) [S]-[C]→
- AIR FUEL RATIO (5) [S]-[A]-[Cat]-[A]→ $O_2$ MEASUREMENT BEFORE AND AFTER CATALYTIC COMBUSTION
$CO+O_2 \rightarrow CO_2$
$HC+O_2 \rightarrow CO_2+H_2O$
- $O_2$ CONCENTRATION
- AIR FUEL RATIO (LEAN SIDE RELATIVE TO THEORETICAL AIR FUEL RATIO)
- COMBUSTION EFFICIENCY (6) [S]-[A]-[B]→ COMPARISON BETWEEN $O_2$ MEASUREMENTS WITH OR WITHOUT CATALYTIC ACTION
$CO+O_2 \rightarrow CO_2$
$HC+O_2 \rightarrow CO_2+H_2O$
- $O_2$ CONCENTRATION
- AIR FUEL RATIO (LEAN SIDE RELATIVE TO THEORETICAL AIR FUEL RATIO)
- COMBUSTION EFFICIENCY (7) [S]-[A]-[C]→
- $O_2$ CONCENTRATION
- AIR FUEL RATIO
- COMBUSTION EFFICIENCY FIG. 5 (1)
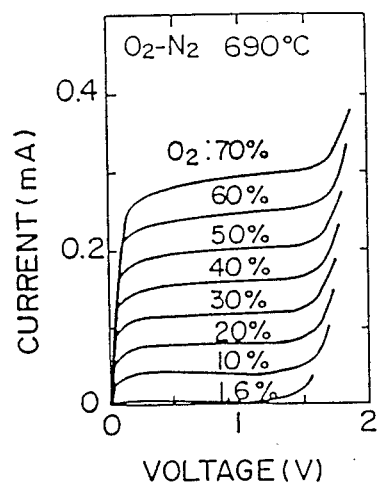
FIG. 5 (2)
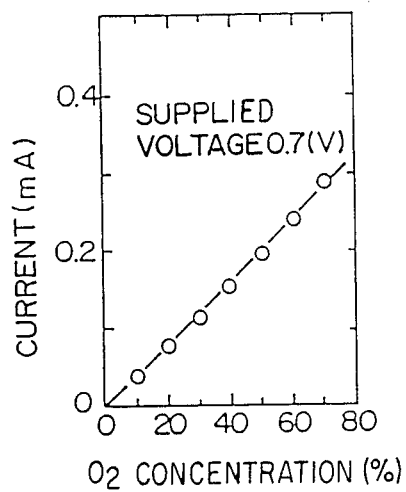
FIG. 6
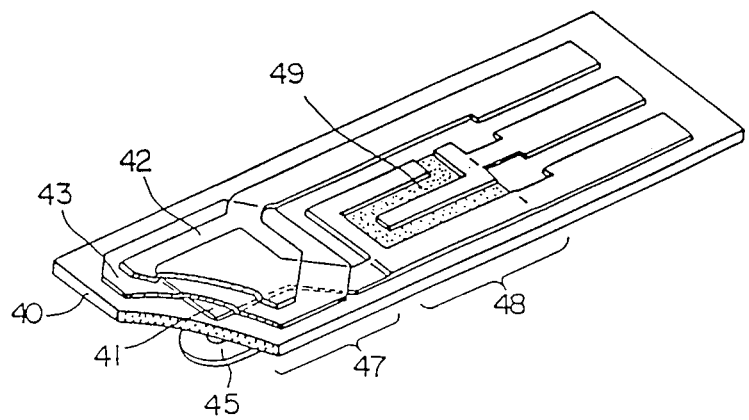

FIG. 9 (1)
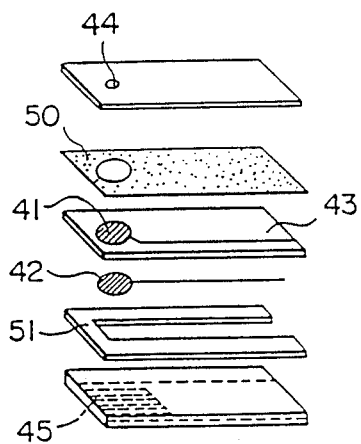
FIG. 9 (2)
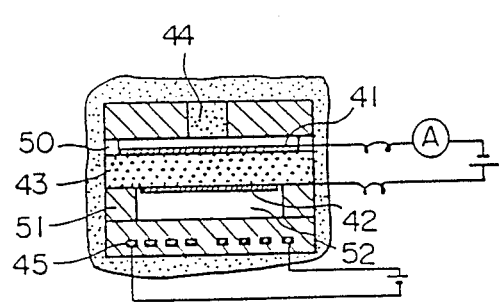
FIG. 10
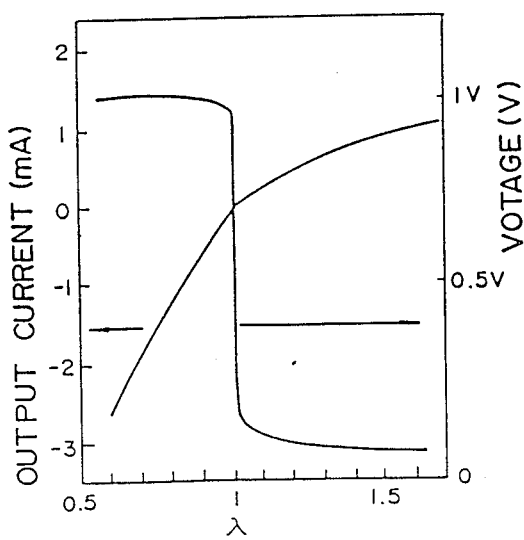

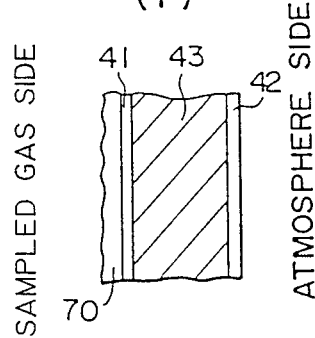
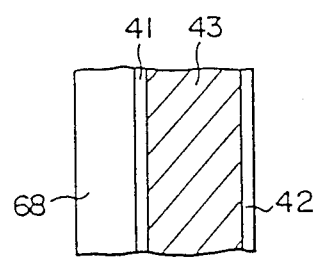
FIG. 11 (1)
FIG. 11 (2)

GAS SAMPLING VALVE

BACKGROUND OF THE INVENTION

1. Field of the Invention

This invention relates generally to gas sampling valves and, more particularly, to a gas sampling valve for sampling gas in an engine or a combustion system so as to perform local composition measurement.

2. Discussion of the Background

A gas sampling technique is known as a means for measuring the concentration of local gases, or the air excess ratio $\lambda$ or air fuel ratio of an air-fuel mixture in a cylinder of an internal combustion engine or in a combustion system. This gas sampling technique is used to measure the distribution of the excess air ratio of an air-fuel mixture directly relating to exhaust components including $No_x$, HC and soot in order to improve the performance of engines such as gasoline and diesel engines. In an example of this gas sampling technique such as the one disclosed in SAE Paper 750849, an electromagnetic drive type of gas sampling valve having a gas sampling inlet faced to a combustion chamber is mounted on a cylinder head of an engine, and the gas sampling inlet of the gas sampling valve is opened in synchronization with the rotation of the engine by a predetermined crank angle, thereby taking a small quantity of gas out of the combustion chamber. This small quantity of gas taken out by the gas sampling valve is supplied to a gas analyzer such as gas chromatography directly or indirectly after being stored in a storage vessel, and is thereby analyzed.

In this case, the measurement of the air excess ratio and combustion efficiency is possible only after the measurement and analysis of all of various components in the gas.

SAE Paper 850044 shows the technique of measuring only the air excess ratio based on the concentration of $CO_2$ after burning the gas using a catalyst. This method, however, needs a large quantity of gas and thus needs a device for storing such gas. Further, great care must be taken in exchanging or sealing the gas to maintain measurement accuracy. Furthermore, the analyzed and the whole system are of a large size.

Thus, in the above-mentioned conventional techniques, the gas sampling and the analysis cannot be performed simultaneously. Further, in these conventional gas sampling techniques, measurement of gas is performed chiefly with respect to targeted gases in order to fully analyze gases in cylinders of an engine. Even in the case of measurement for simply determining the air excess ratio, a large amount of sampled gas is needed and the gas sampling operation must be repeated over several tens to several thousands of cycles. There are therefore problems of time lag between sampling and analysis and durability of the gas sampling valve. Moreover, in the process of transferring the sampled gas by means of the storage vessel or transference pipe, there is a possibility of external air entering the gas if the gas leaks. There is thus a problem of difficulty in the accuracy of analysis.

As mentioned above, measurement of local air excess ratio is important in the study of engines. However, the above-described gas sampling technique requires a long time for analysis and is defective in terms of accuracy. It also requires a high-cost gas analyzer which needs to be operated with a complicated analyzing technique. Therefore, these gas sampling techniques are not generally used.

SUMMARY OF THE INVENTION

The present invention has been achieved overcoming these problems, and an object of the present invention is to provide a gas sampling valve which enables the local measurement of the concentration of gases, air excess ratio and combustion efficiency which are important in the study of engines to be performed with accuracy in a simple manner.

To this end, the present invention provides a gas sampling valve comprising: a housing having a small opening for gas sampling and a gas flow passage one end of which communicates with the outside and the other end of which communicates with the small opening; a valve for opening and closing the small opening; an operating mechanism for operating the valve; and at least one detector for detecting the concentration of components of sampled gas, disposed in the gas flow passage at a short distance from the small opening.

The detectors to be used include lean $\lambda$ sensors with and without catalytic activity, and wide-range air fuel ratio sensors with or without catalytic activity.

The principle of air excess ratio measurement of combustion gas and the principle of rough calculation of combustion efficiency based on the oxygen concentration will be described below. The principle of measurement of the air excess ratio and the oxygen concentration of combustion gas will first be described. FIG. 1 schematically shows the composition of a combustion gas. Let $C_T$ represent the converted concentration of a combustible gas stoichiometrically equivalent to oxygen. While suffix X is attached to each components of the combustion gas, the converted concentration $C_T$ is expressed by equation 1:

$$C_T = \frac{1}{2}[CO]_x + \frac{1}{2}[H_2]_x + \left(m + \frac{n}{4}\right)[C_mH_n]_x \quad (1)$$

where [ ] represents the volumetric concentration of each component of the combustion gas; and $C_mH_n$ represents the averaged fuel composition.

In the case of incomplete combustion, the composition of the combustion gas relative to the air excess ratio $\lambda$ cannot be determined definitely since the fuel composition in equation 1 differs depending upon the degree of combustion. Therefore, in the case of incomplete combustion, the air excess ratio $\lambda$ cannot be measured from the concentration of the combustion gas. In the case of $\lambda \geq 1$, if combustion gas formed by incomplete combustion is completely oxidized by an oxidization catalyst, the concentration after this reaction is as indicated by the broken line on the lean side in FIG. 1. In the case of $\lambda < 1$, if the residual oxygen in the combustion gas is completely burnt, the concentration is as indicated by the broken line on the rich side in FIG. 1. Thus, a gas composition which can be definitely determined by the air excess ratio $\lambda$ is provided. Therefore, if the concentration of the combustion gas after complete oxidation reaction by a catalyst is detected by a $\lambda$ sensor, an output from the $\lambda$ sensor is determined, and then from this output the air excess ratio can be measured. The air excess ratio exhibited at this point corresponds to the concentration of oxygen at $\lambda = 1$ and on its lean side and corresponds to the fuel concentration on its rich side.

Conversely, if the λ sensor having no catalytic properties contacts the combustion gas before catalytic action, namely, the combustion gas formed by incomplete combustion, an output from the λ sensor corresponds to the concentration of oxygen in the detected gas, and the combustion efficiency can be examined by the comparison between this concentration and the above-mentioned concentration of oxygen measured after catalytic action.

Next, the principle of rough calculation of combustion efficiency will be described below. The combustion efficiency is defined as the ratio of the calorific value of a fuel in complete combustion and a calorific value in a certain state of combustion. However, since the calorific value in combustion cannot be measured directly, the combustion efficiency is, in this case, estimated by calculation from the concentration of oxygen consumed by the combustion. If the combustion efficiency is $\eta_{comb}$, $$\eta_{comb} = \frac{H_0 - H_1}{H_0} \quad (2)$$

where $H_0$ represents a lower calorific value of the fuel; and $H_1$ represents the calorific value of an incomplete combustion part of the combustion gas.

The calorific value $H_1$ is in Correspondence with $C_T$ in equation 1. To be exact, however, the calorific values of CO, $H_2$, and $C_mH_n$ differ from each other so that the exact calorific value is different from an estimated value of $H_1$ obtained by multiplying $C_T$ stoichiometrically equivalent to $O_2$ by an average calorific value. In this case, however, the calorific value will be approximately estimated as a degree of reaction with $O_2$. Let suffix 0 be attached to the concentration of oxygen in initial air-fuel mixture and suffix y to components sufficiently burnt by the catalyst. The, a ratio $\eta_1$ is defined by equation 3:

$$\eta_1 = \frac{[O_2]_0 - \alpha[O_2]_x}{[O_2]_0 - \beta[O_2]_y} \quad (3)$$

where [ ] represents the volumetric concentration; and α and β are coefficients which modify a change in the total number of mols over the states before and after the combustion.

If the composition of air includes only $N_2$ and $O_2$, and if the ratio thereof is $N_2$: $O_2 = 0.79:0.21$, $$[O_2]_0 = \frac{\lambda\left(m + \frac{n}{4}\right)}{1 + \lambda\left(m + \frac{n}{4}\right)\left(1 + \frac{0.79}{0.21}\right)} \quad (4)$$

when $\lambda < 1$, $[O_2]_y = 0$ when $\lambda \geq 1$, $[O_2]_y =$ \quad (5)

$$\frac{(\lambda - 1)\left(m + \frac{n}{4}\right)}{\frac{n}{4} + \lambda\left(m + \frac{n}{4}\right)\left(1 + \frac{0.79}{0.21}\right)}$$

In place of $[O_2]_y$, an actual value measured after catalytic reaction may be used.

The original reaction formula is when λ < 1.

$$C_mH_n + \lambda\left(m + \frac{n}{4}\right)O_2 \rightarrow$$

$$m \cdot \lambda \cdot CO_2 + \frac{n}{2} \cdot \lambda \cdot H_2O + (1 - \lambda)C_mH_n$$

when λ ≥ 1, $$C_mH_n + \lambda\left(m + \frac{n}{4}\right)O_2 \rightarrow$$

$$m \cdot CO_2 + \frac{n}{2}H_2O + (\lambda - 1)\left(m + \frac{n}{4}\right)O_2$$

Let the reaction formula of the combustion gas be $$C_mH_n + \lambda\left(m + \frac{n}{4}\right)O_2 \rightarrow$$

$$a \cdot CO + b \cdot CO_2 + c \cdot H_2 + d \cdot H_2O + e \cdot C_mH_n + f \cdot O_2$$

Then,

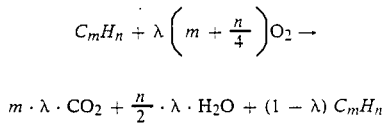

and α and β are represented by

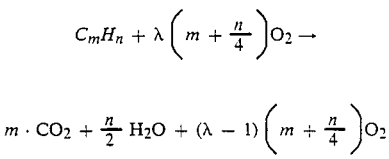

$[O_2]_x$ in equation 6 can be measured, but a, b, c, d, e, and f cannot be measured. Therefore, it is not possible to strictly determine α. However, the change in the total number of mols of the combustion gas is comparatively small, and it is therefore possible to suppose α=β in practice.

On the other hand, let $\eta_2$ represent the ratio of a calorific value obtained when $O_2(\lambda<1)$ or fuel $(\lambda\geq 1)$ is completely consumed by the combustion to the calorific value of the fuel. Then, when λ<1, $\eta_2=\lambda$ when λ≥1, $\eta_2=1$ \quad (9)

The combustion efficiency is approximately

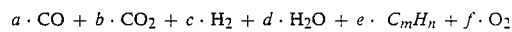

and it can be calculated from concentration of oxygen measured before and after the cataltic combustion.

Calculation of the combustion efficiency is not limited to the above equations and the accuracy of calculation can be improved by experiment and theoretical development and by the use of more suitable empirical equations, so long as the measurement and calculation are based on oxygen concentration detection using the $\lambda$ sensor.

As described above, information on the oxygen concentration, air excess ratio, combustion efficiency, and so forth can be obtained by the combination of the $\lambda$ sensor and the oxidation catalyst. In accordance with the present invention, therefore, one or more detectors (sensor) adapted to detect the oxygen concentration or combustion gas concentration is provided in a gas flow passage of the gas sampling valve. These detectors can be disposed in various ways for measurement of the oxygen concentration, the air excess ratio and the combustion efficiency, as represented by arrangements 1 to 7 shown in FIG. 2. The arrangements shown in FIG. 2 include gas sampling valves S, and $\lambda$ sensors A, B, C and D disposed in gas flow passages of the gas sampling valves. The sensor A is a lean $\lambda$ sensor having substantially no catalytic activity; the sensor B is a lean $\lambda$ sensor having catalytic activity; the sensor C is a wide-range air fuel ratio sensor having catalytic activity; and the sensor D is a wide-range air-fuel ratio sensor having substantially no catalytic activity. The arrangements also include a catalyst represented by Cat.

FIG. 2(1) shows an arrangement setup for the purpose of measuring the oxygen concentration in the sample gas having stoichiometric air fuel ratio or leaner. The sensor A has to be replaced by the sensor D when the measurement is to be conducted over the entire region including also the region richer than the stoichiometric mixture. Arrangements shown in FIGS. 2(2) and 2(3) are used for the purpose of measuring the air excess ratio in the stoichiometric and leaner regions. The sensor A has to be replaced by the sensor D when the measurement is to be conducted over the entire region including also the region richer than the stoichiometric mixture. When it is desired to measure all the oxygen concentration, air fuel ratio and the combustion efficiency, arrangements shown in FIGS. 2(5) and 2(6) are suitably used when the measurement has to cover only the stoichiometric and leaner regions. When the measurement has to cover the entire region including the richer side, an arrangement shown in FIGS. 2(5) and 2(7) is suitably used in which the sensor A has been replaced by the sensor D. In the case of the arrangements 6 and 7 in FIG. 2, the order of the sensors A and B or D and C may be reversed.

In accordance with the present invention, as described above, the detector for detecting the oxygen concentration or the combustion gas concentration is disposed in the gas flow passage of the gas sampling value, thereby enabling the oxygen concentration, air excess ratio, combustion efficiency, and so forth to be measured with accuracy in a simple manner with a small amount of gas and without using any ordinary analyzer requiring a large amount of the sampling gas.

It is also to be pointed out that there is no need for temporary storage of the sample gas, and the measurement can be conducted in an on-line manner, so that a phenomenon taking place in a transient period after the start-up of the engine can be measured advantageously.

BRIEF DESCRIPTION OF THE DRAWINGS

FIG. 2 is a block diagram of combinations of gas sampling valves and sensors disposed in the gas sampling valves;

FIG. 5(1) is a diagram of current-voltage characteristics of a limiting current oxygen sensor;

FIG. 5(2) is a diagram of a current-oxygen concentration characteristic of a limiting current oxygen sensor;

FIG. 6 is a perspective view of a $\lambda=1$-lean-integrated air fuel sensor;

FIGS. 9(1) and 9(2) are an exploded perspective view and a cross sectional view of a wide-range air fuel ratio sensor;

FIG. 10 is a diagram of a relationship between $\lambda$ and a current output from an atmosphere introduction type of wide-range air fuel ratio sensor;

FIGS. 11(1) and 11(2) are enlarged cross-sectional views of specific structures of the sensor in accordance with the present invention;

FIG. 13(2) is a diagram of a opening-closing timing of the gas sampling valve;

DESCRIPTION OF THE PREFERRED EMBODIMENTS

Figure 1:
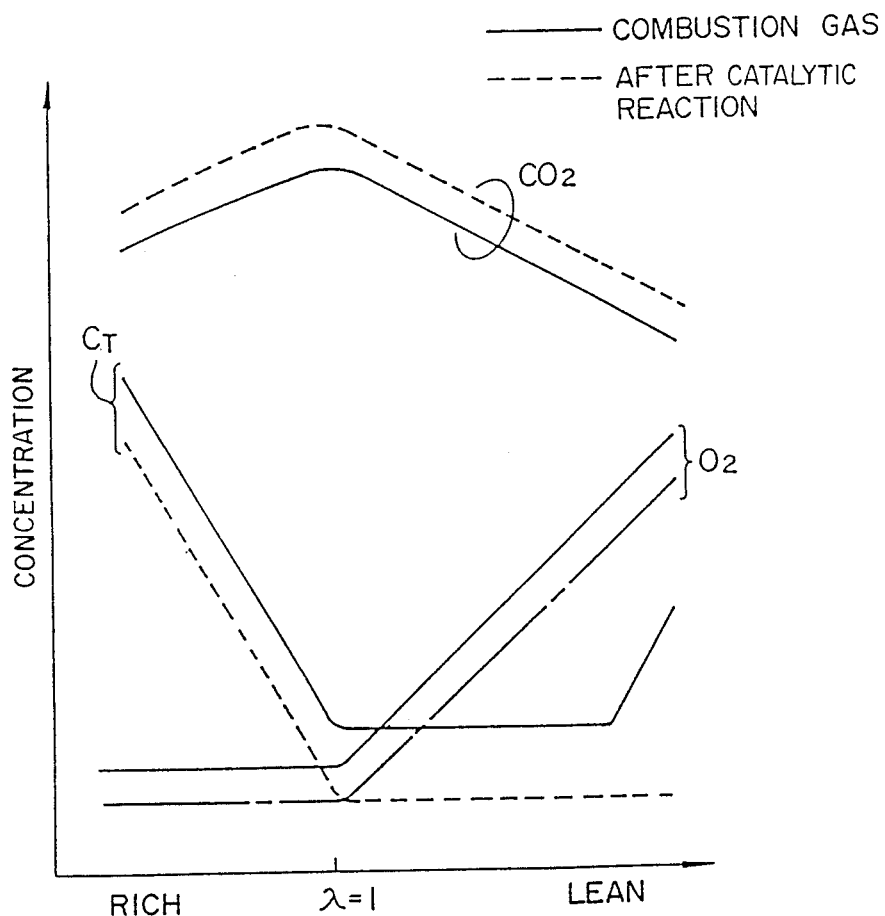
FIG. 1 is a diagram of comparison between compositions of combustion gas with respect to a case in which there is no catalytic reaction and a case in which catalytic reaction takes place.
Figure 3:
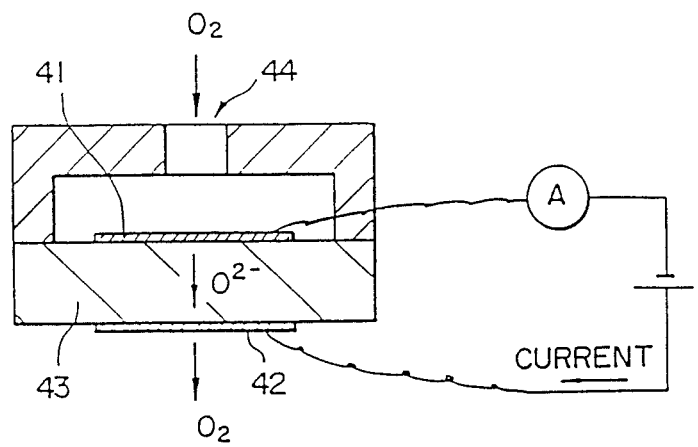
FIG. 3 is a cross-sectional view of a limiting current oxygen sensor using a body having an opening.
Figure 4:
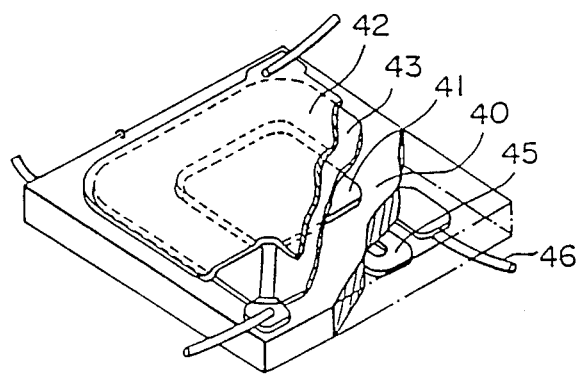
FIG. 4 is a perspective view of a limiting current oxygen sensor using a porous body.

The present invention will be described below in detail with respect to preferred embodiment thereof with reference to the accompanying drawings. Referring to FIGS. 3 to 10, a sensor which can be applied to embodiments of the present invention will first be described. FIG. 3 shows a limiting current type of oxygen sensor which can be applied to sensors A and B in FIG. 2. This sensor has a zirconia solid electrolyte 43 pinched between a cathode 41 and an anode 42. A cover with small opening 44 is disposed over the cathode 41. The cathode 41 and the anode 44 are connected to a power source. When a current flows through the zirconia solid electrolyte 43, oxygen flows thereinto from the cathode 41 and is discharged from the anode 42. The small opening 44 formed in the cover functions to regulate the speed at which oxygen flows into the cathode 44. This regulation of the flow of oxygen effected by the small opening 44 forms a range in which the current is saturated at a certain level even if the voltage is increased, as shown in FIG. 5(1). Since this level of current (limiting current) is proportional to the concentration of oxygen, the concentration of oxygen can be measured from the current if a constant voltage is applied. FIG. 4 shows a sensor which is of a practical type based on the limiting current type of oxygen sensor shown in FIG. 3, and in which a porous alumina substrate 40 is used as an oxygen gas regulating member in place of the small opening 44, and a cathode 41 formed from platinum, a zirconia solid electrolyte 43, an anode 42 formed from platinum are successively superposed on each other over one surface of the porous alumina substrate 40. A heater 45 formed from platinum is laid over the other surface of the porous alumina substrate 40, thereby enabling the sensor to be heated at a constant temperature. The limiting current oxygen sensor shown in FIGS. 3 and 4 exhibits current-voltage characteristics such as those shown in FIG. 5(1), and exhibits a current-oxygen concentration characteristic such as that shown in FIG. 5(2). It is thereby possible to measure the concentration of oxygen in the sampling gas from the value of the current flowing through the sensor.

Figure 7:
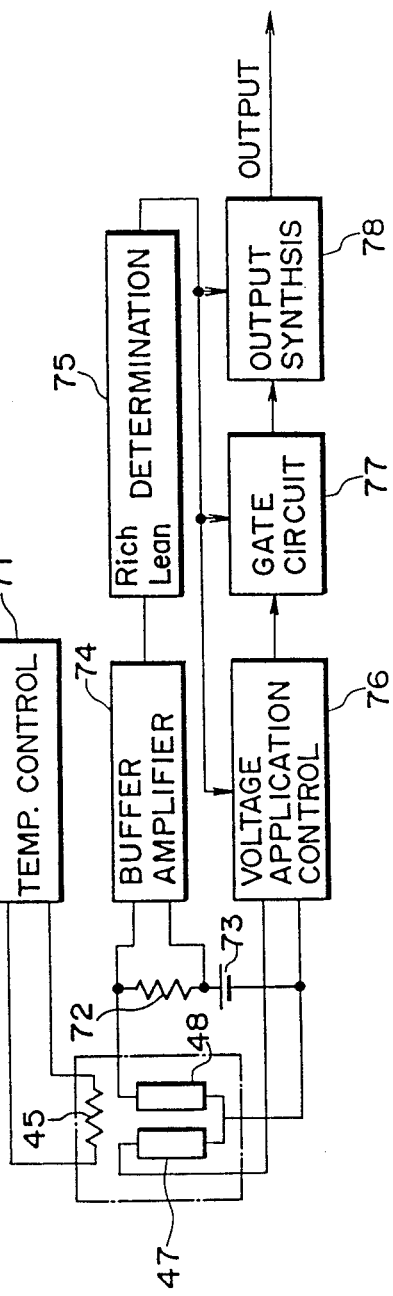
FIG. 7 is a block diagram of a detection processing circuit adapted to the sensor shown in FIG. 6.
Figure 8:
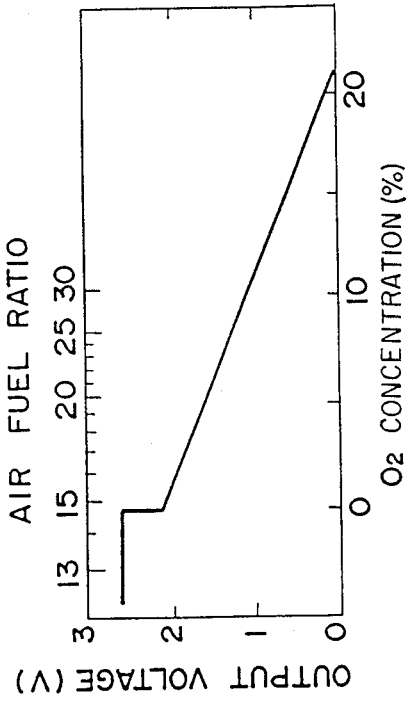
FIG. 8 is a diagram of an output from the circuit shown in FIG. 7.

FIG. 6 shows a $\lambda=1$-lean-integrated air fuel ratio sensor which can be applied to sensors A and B in FIG. 2. This sensor is constituted by integrating a lean detection section 47 having a structure similar to that of the above-described limiting current oxygen sensor with a $\lambda=1$ detection section 48 for detecting a theoretical air fuel ratio ($\lambda=1$). The lean detection section 47 is constructed by successively superposing a cathode 41 formed from platinum, a zirconia solid electrolyte 43, an anode 42 formed from platinum over a porous alumina substrate 40, as described above with respect to the limiting current oxygen sensor. The $\lambda=1$ detection section 48 is constructed as a resistance varying type of $\lambda=1$ sensor having an oxide semiconductor 49 whose resistance abruptly changes at $\lambda=1$ by a value ranging from 3 to 5 places and which is laid over a surface of porous alumina substrate 40. A heater 45 formed from platinum is laid over the other surface of the porous alumina substrate 40, thereby enabling the $\lambda=1$-lean-integrated air fuel ratio sensor to be heated at a constant temperature. In this sensor, outputs from the lean detection section 47 and the $\lambda=1$ detection section 48 differ from each other and, therefore, a sensor signal processing circuit such as that shown in FIG. 7 is added. This sensor signal processing circuit is constituted by a temperature control circuit 71, a reference resistor 72, a power source 73, a buffer amplifier 74, a rich-lean determination circuit 75, a voltage application control circuit 76, a gate circuit 77, and an output synthesis circuit 78. The voltage of a signal output from the output synthesis circuit 78 starts to change at the theoretical air fuel ratio, as shown in FIG. 8, and changes in accordance with the oxygen concentration in a range on the lean side of the theoretical air fuel ratio. In the case of the above-described limiting current oxygen sensor, the air fuel ratio can be measured only in a lean range. In contrast, the $\lambda=1$-lean-integrated air fuel ratio sensor the lean air fuel ratio to be measured from $\lambda=1$.

A wide-range air fuel ratio sensor will be described with reference to FIGS. 9(1) and 9(2). This sensor can be applied to sensors C and D in FIG. 2. In this sensor, the atmospheric air is introduced to the side of an anode 42 which serves as a reference pole while a small opening 44 for regulating the speed at which oxygen flows into the sensor is formed in a cathode 41. When a constant voltage is applied between the anode 42 and the cathode 41, oxygen gas moves by oxygen pumping action from the cathode 41 to the anode 42 if a lean atmosphere is provided on the side of the cathode 41. A current thereby flows from the anode 42 to the cathode 41. However, when the anode atmosphere becomes a rich atmosphere, a voltage, which acts to cancel the voltage which has been applied between the anode 42 and the cathode 41, occurs between these electrodes by galvanic action. As a result, only a voltage, which corresponds to the difference between the voltage (about 1V) generating between the cathode and the anode by the formation of the rich atmosphere on the cathode 41 nd the voltage (about 0.6V) that has been applied to the anode and the cathode, is applied between the cathode and the anode. As a consequence, oxygen gas flows by a pumping action into the cathode (atmosphere standard), thereby exhibiting $\lambda$-output current characteristics as shown in FIG. 10. Therefore, this wide-range air fuel ratio sensor enables the concentration of oxygen gas to be continuously measured from rich to lean atmospheres. The air fuel ratio can be measured from the concentration of oxygen gas.

All of the above-described air fuel ratio sensors are coated with a porous coating material (e.g., oxide such as alumina or silica gel having heat-resistant properties) in order to protect the sensors from mechanical impacts or the sensors when the sensors are actually used. Accordingly, it is possible to vary the state of the gas reaching the electrode of the sensor by changing the structure or composition of the porous body. That is, the sensor can be supplied with a gas which is produced by complete reaction effected by heightened catalytic activity, or it is supplied with a gas in a state of incomplete reaction by lowering the catalytic activity. To heighten the catalytic activity in this method, a simple substance selected from noble metals (metal having high catalytic activity) such as Pt, Rh, Pd, etc., or a mixture of these metals is added to or mixed into the porous body and a portion of the small opening (in the case of the sensor B shown in FIG. 2). To lower the catalytic activity, it is sufficient to coat the sensor (e.g., the sensor A shown in FIG. 2) with a porous coating material. The effect can be further improved by reducing the sensor heating temperature.

In the case of the wide-range air fuel ratio sensor, a coating material 70 which exhibits substantially no catalytic activity is applied over the surface of the exhaust-side cathode 41 to provide the sensor D, or a coating material 70 having a markedly high catalytic activity is applied over the surface of the exhaust-side cathode 41 to provide the sensor C, as shown in FIG. 11(1). In the case of the limiting current oxygen sensor, a substance which exhibits substantially no catalytic activity is used to constitute a small opening or porous body 68 (corresponding to the porous alumina substrate 40 and the small opening 44), thereby providing the sensor A, while a substance having markedly high catalytic activity is used to constitute or is supported on the small opening or the porous substrate 68, thereby providing the sensor B, as shown in FIG. 11(2).

Figure 12:
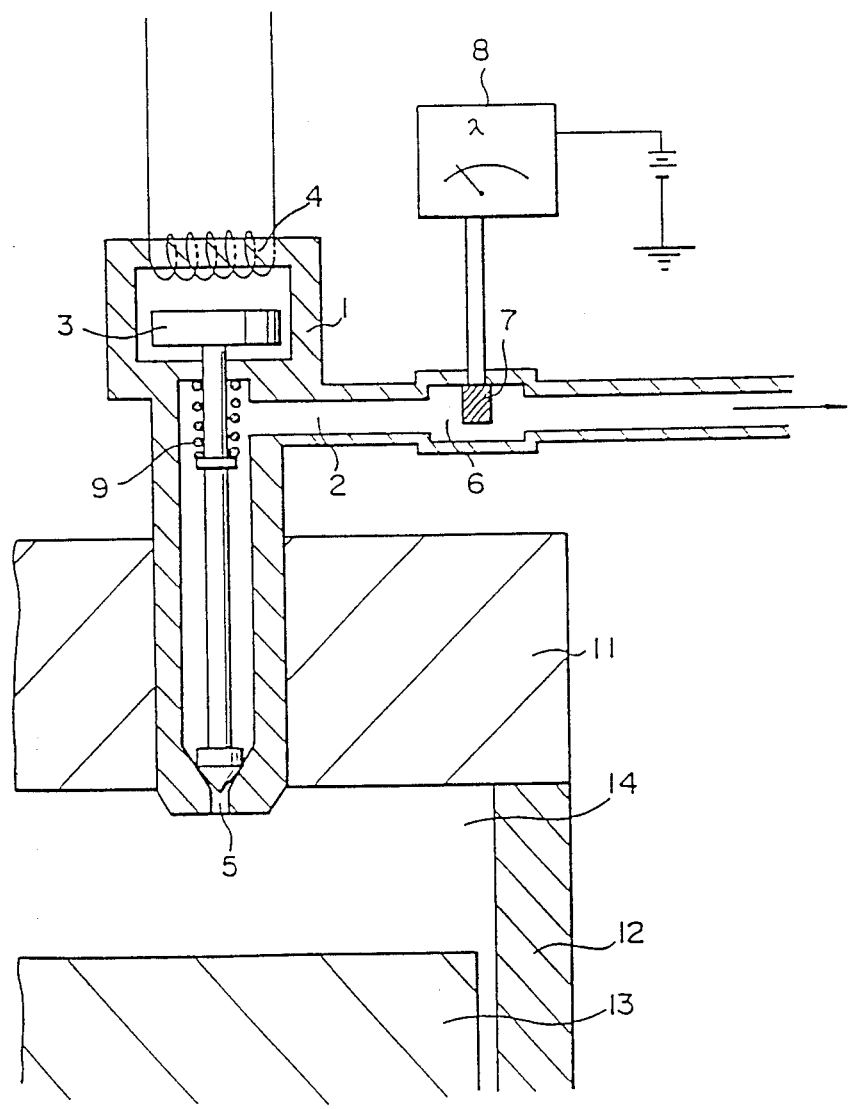
FIG. 12 is a cross-sectional view of a portion of an embodiment of the present invention in the vicinity of the gas sampling valve.

The present invention will now described with respect to a gas sampling valve which has the above-described type of $\lambda$ sensor and which represents an embodiment of the present invention. As shown in FIG. 12, a housing 1 has a gas sampling inlet 5 formed at its extreme end, and a gas flow passage 2 is formed inside the housing 1 such that it provides communication between the gas sampling inlet and the exterior. A valve rod 3 (in this example, a needle valve) for opening or closing the gas sampling inlet 5 is axially movably disposed in the gas flow passage 2 on the side of the gas sampling inlet 5. The valve rod 3 is constantly urged by a spring 9 in the direction of operation of closing the gas sampling inlet 5. An electromagnetic coil 4 is disposed in the vicinity of a root portion of the valve rod 3. When the electromagnetic coil 4 is energized, the valve rod 3 is moved in the axial direction against the urging force of the spring 9, thereby opening the gas sampling inlet 5. A sensor attachment portion 6 is formed in the gas flow passage on the exterior side by slightly widening the gas flow passage 2, and a small $\lambda$ sensor 7 is attached to the sensor attachment portion 6. The $\lambda$ sensor 7 is connected to a $\lambda$ output meter 8 which is connected to a power source. The length of a portion of the housing 1 constituting the gas flow passage 2 between the sensor attachment portion 6 and the exterior is determined in such a manner that it can prevent the atmospheric air from reversely flowing into the sensor attachment portion 6.

Figure 13:
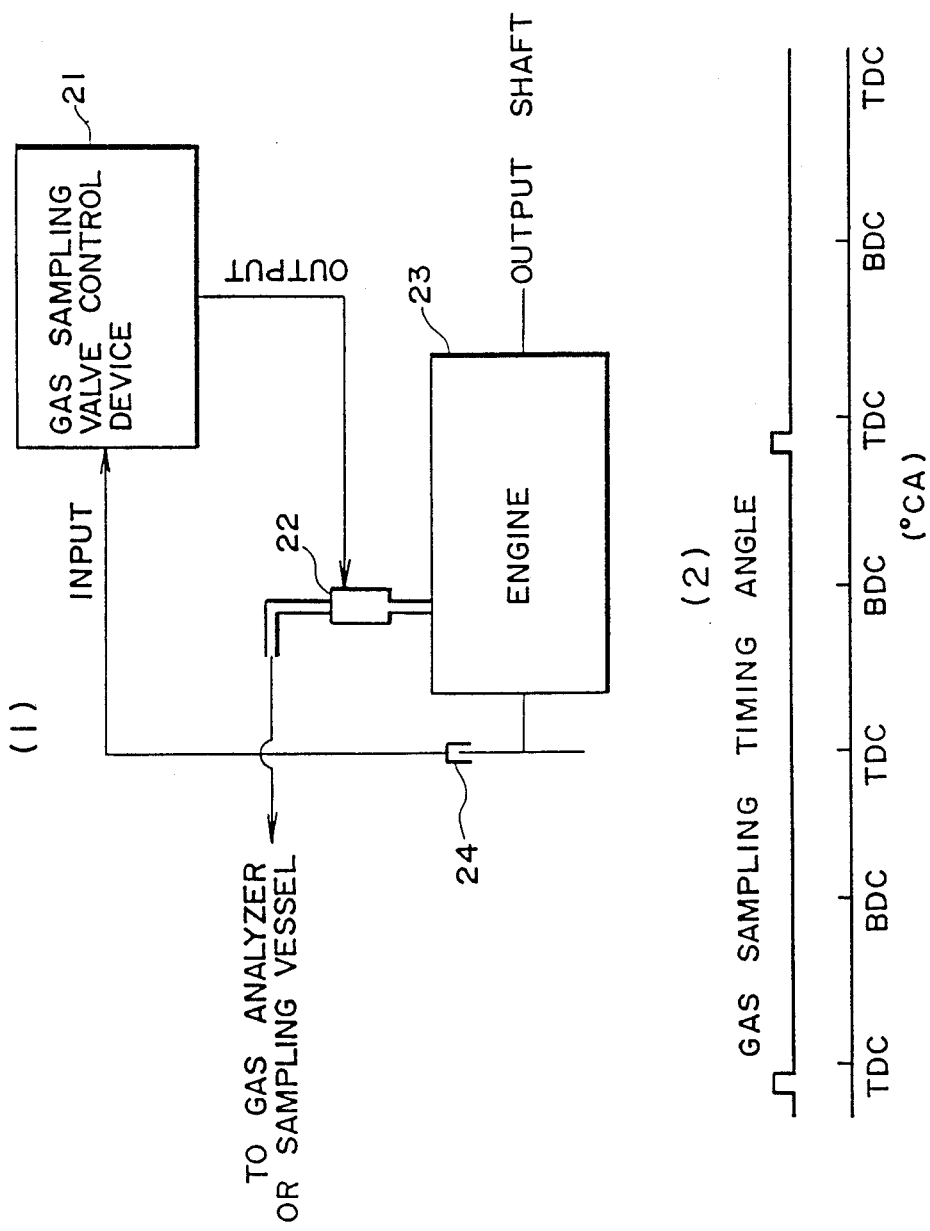
FIG. 13(1) is a diagram of a control system in which the gas sampling valve is attached to an engine.

The thus-constructed gas sampling valve is mounted on a cylinder head 11 in such a manner that its main body passes through the cylinder and the gas sampling inlet 5 faces to or projects into the interior of the combustion chamber 14. Reference characters 12 indicates a cylinder block and reference character 13 a piston. The electromagnetic coil 4 is, as shown in FIG. 13, connected to a gas sampling valve control circuit 21 while an exterior end of the housing is connected to a gas analyzer or a gas sampling vessel, if the analysis of the gas is needed. A crank angle sensor 24 which is adapted to determine the opening-closing timing of a gas control valve by energizing the electromagnetic coil 4 of the gas sampling valve 22 is connected to the gas sampling valve control circuit 21.

The operation of this embodiment will be described below. The gas sampling valve 22 is opened or closed by the gas sampling valve control circuit 21 in synchronization with a signal from the crank angle sensor 24 mounted on an engine 23. An example of the opening-closing timing of this operation is shown in FIG. 13(2). This exemplifies a case of a 4-stroke-cycle engine. By this timing, gas is sampled one time during two revolutions of the engine at the same crank angle (in FIG. 13 (2), a predetermined crank angle in advance of the top dead center). If it is important to consider the thermal load of the electromagnetic coil 4 of the gas sampling valve 22, gas sampling may be performed by energizing the electromagnetic coil at intervals of several cycles. Thus, the electromagnetic coil 4 is energized in synchronization with the crank angle by a drive signal output from the gas sampling valve control circuit 21, the valve rod 3 is driven by the magnetic force of the electromagnetic coil 4 against the urging force of the spring 9 so as to open the gas sampling inlet 5, thereby introducing high-temperature gas in the combustion chamber 14 of the engine into the gas flow passage 2 through the gas sampling inlet 5. The gas received in the gas flow passage 2 flows inside the gas flow passage 2 by the internal pressure of the combustion chamber 14 and moves to the sensor attachment portion 6. The air excess ratio $\lambda$ is detected by the $\lambda$ sensor 7 at the sensor attachment portion 6, and the air excess ratio thereby detected is instantaneously displayed by being supplied as an electrical signal to the $\lambda$ output meter 8. After passing through the sensor attachment portion 6, the gas is stored in the gas sampling vessel or is supplied to the gas analyzer via a reference pipe if the gas analysis is needed. The arrangement shown in FIG. 12 exemplifies the dispositions 1, 2, and 3 shown in FIG. 2. As described above, the oxygen concentration, the air excess ratio, and so forth can be measured simultaneously with gas sampling.

In accordance with this embodiment, as described above, the small $\lambda$ sensor is attached to the flow passage of the electromagnetic type of gas sampling valve, and the air excess ratio can be detected from a small quantity of sampled gas, thereby eliminating the need for a complicated technique for gas analysis as well as reducing the time taken to perform the analysis. In the case of detection of the air excess ratio, there is no possibility of a leak of gas throughout the passage from sampling to analysis, thereby improving the accuracy of the data. Data on the air excess ratio can be instantaneously obtained simultaneously with gas sampling. There is therefore no need for calculation of the air excess ratio, enabling a reduction in the size of the system as well as reduction in cost.

Figure 14:
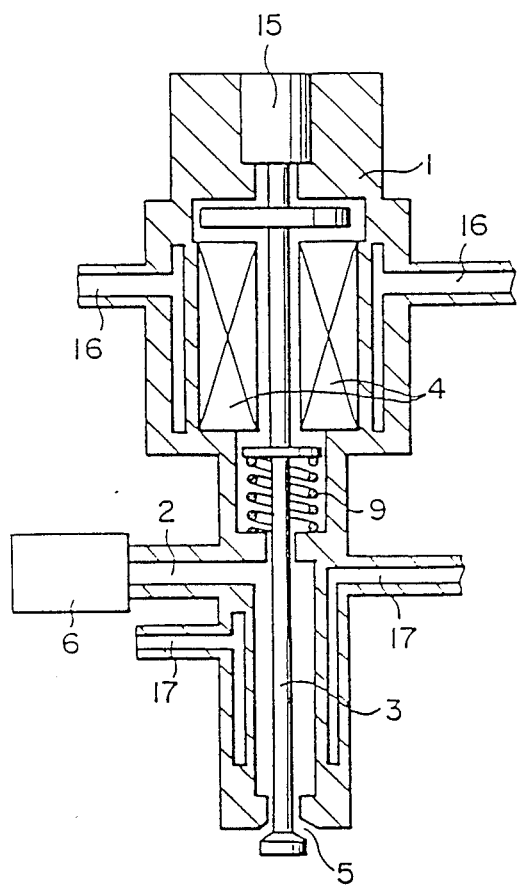
FIGS. 14 and 15 are cross-sectional views of a gas sampling valve which represents other embodiments of the present invention.
Figure 15:
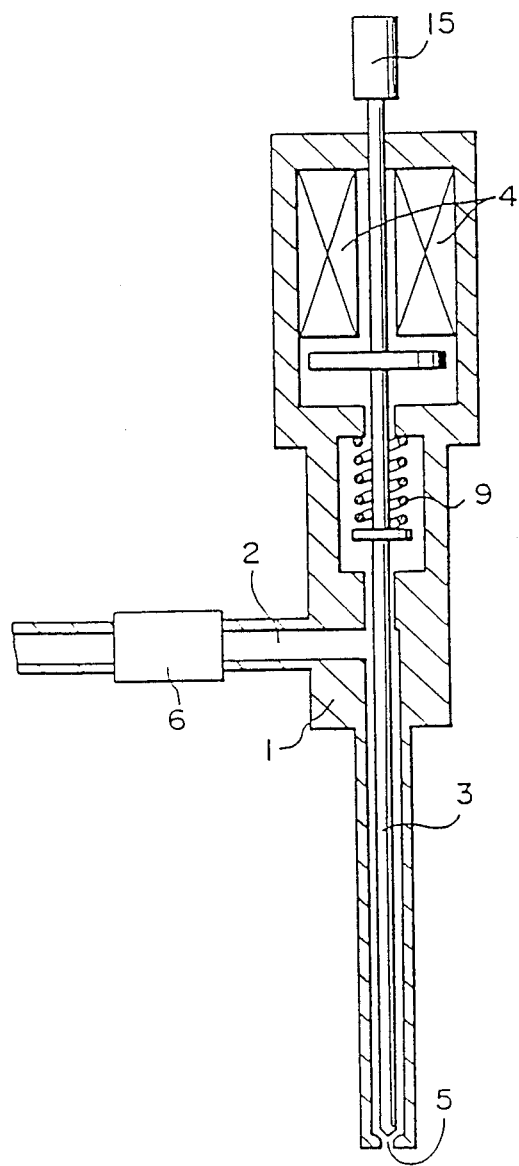

Another embodiment of the present invention will be described below with reference to FIGS. 14 to 15. A gas sampling valve shown in FIG. 14 is substantially the same as the one shown in FIG. 12. Corresponding portions in this embodiment are indicated by the same reference characters and description for them are not repeated. The gas sampling valve shown in FIG. 14 differs from the gas sampling valve shown in FIG. 12 in that the former is of an opening out type and has a valve rod 3 which opens outside a gas sampling inlet 5 by an electromagnetic force. This gas sampling valve is provided with a lift sensor 15 for detecting the lift of the valve rod 3, channels 16 for cooling water used to cool an electromagnetic coil 4, and channels 17 for cooling water used to cool sampled gas. On the other hand, a gas sampling valve shown in FIG. 15 is of a opening in type and has a valve rod 3 which opens inside a gas sampling inlet 5 by an electromagnetic force, as in the case of the gas sampling valve shown in FIG. 12.

Figure 16:
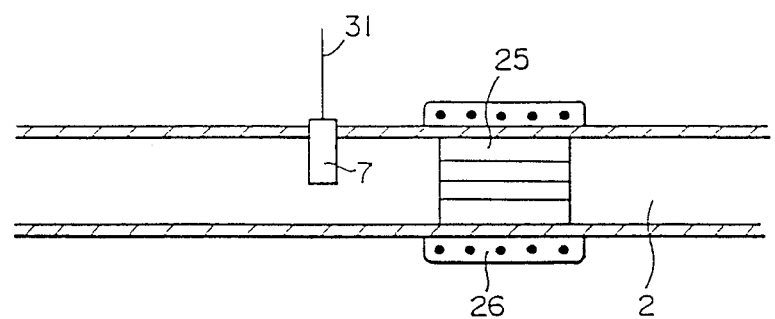
FIGS. 16, 17, and 18 are cross-sectional views of details of the sensor attachment portions of the above gas sampling valves.

Next, the structures of sensor attachment portions 6 of the gas sampling valves shown in FIGS. 14 and 15 will be described with reference to FIGS. 16 to 18. FIG. 16 shows a sensor attachment portion 6 has the same cross section as that of a gas flow passage 2. Inside the flow passage is disposed a catalyst bed 25 having a monolith carrier on which a noble metal catalyst is carried, and a heater 26 is disposed such that it encircles the catalyst bed 25. The temperature of the catalyst bed 25 is controlled by a heater 26, a temperature detector and a temperature control circuit (not shown) so that the activity of the catalyst is maintained within an active range. A small $\lambda$ sensor 7 which is mounted on the downstream side relative to the catalyst bed 25 is connected to a display device via a lead wire 31. The positional relationship between the catalyst bed and the $\lambda$ sensor shown in FIG. 16 corresponds to the disposition 2 shown in FIG. 2.

Figure 17:
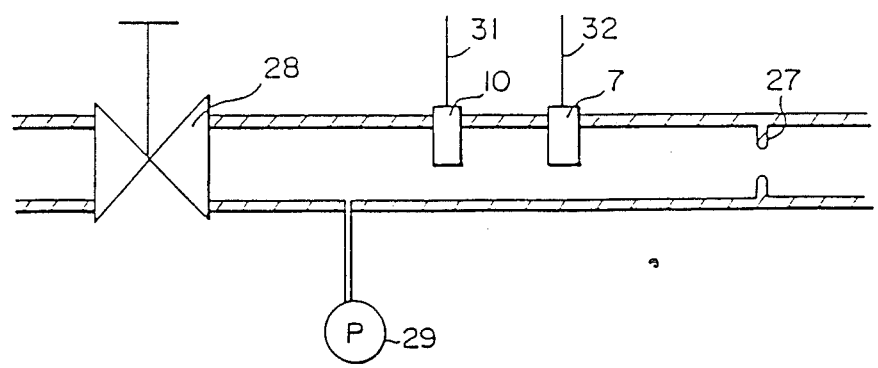

The sensor attachment portion 6 shown in FIG. 17 is constructed in such a manner that a $\lambda$ sensor 7 and a $\lambda$ sensor 10 are disposed between a throttle 27 and a needle valve 28. The pressure inside the sensor attachment portion is controlled on the basis of an output from a pressure gauge 29 so that it is generally constant. This control for achieving a constant pressure in the sensor attachment portion enables a further improvement in the accuracy of the output from the sensor. The combination shown in FIG. 17 corresponds to arrangements 6 and 7 shown in FIG. 2.

Figure 18:
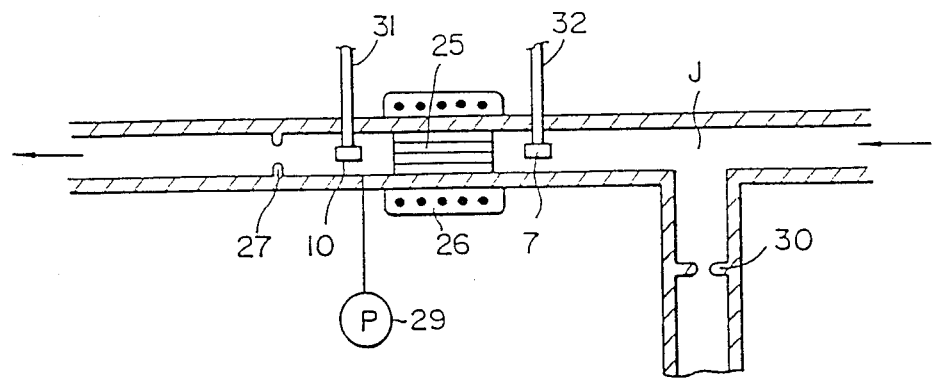

In the arrangement shown in FIG. 18, the flow passage diverges into two branches. One of the branches is ordinarily connected to a gas analyzer while the other branch is used as a sensor attachment portion. Throttle 27 and 30 are respectively provided in these branches, and are used to control the flow rate ratio while and, at the same time, regulate the pressure inside the sensor attachment portion. A three way valve may be provided at the branching portion (portion J in FIG. 18) so as to switch the flow. A catalyst bed 25 of a monolith or capillary type is disposed in the sensor attachment portion. A heater 26 is disposed around the catalyst bed 25. An λ sensor 10 and a pressure gauge 29 are mounted between the heater 26 and the throttle 27. The pressure between the throttle 27 and the catalyst bed 25 is maintained generally constantly by the pressure gauge 29. An λ sensor 7 is disposed upstream relative to the catalyst bed 25. This combination of the sensors and catalyst corresponds to the arrangement 5 of FIG. 2.

In the above-described examples, any type of combination of the throttle and the needle valve is possible. These members are provided for the purpose of preventing the atmospheric air from entering the sensor attachment portion by backflow or diffusion. If the restrictions and the needle valve are not provided, it is necessary to increase the length of the portion of the flow channel extending from the sensor attachment portion to the atmosphere. Each of the above-described examples has been described with respect to only one combination of the sensors and the catalyst, but any type of combination can be selected from those shown in FIG. 2 for each embodiment depending upon the use and purpose intended. It is more preferable to select a catalyst having a high degree of oxidization reaction activity and as well as improved durability. The type of the carrier can be freely selected and the carrier may incorporate a heater. The heater may be of a type for heating gas on the upstream side of the catalyst. Capillary, monolith and pellet types of carrier are applicable as a carrier. It is also possible to use a ceramic heater as a carrier. The sensor attachment portion is not limited to those of the above-described embodiment so long as the temperature and pressure at the sensor attachment portion can be adequately controlled.

Figure 19:
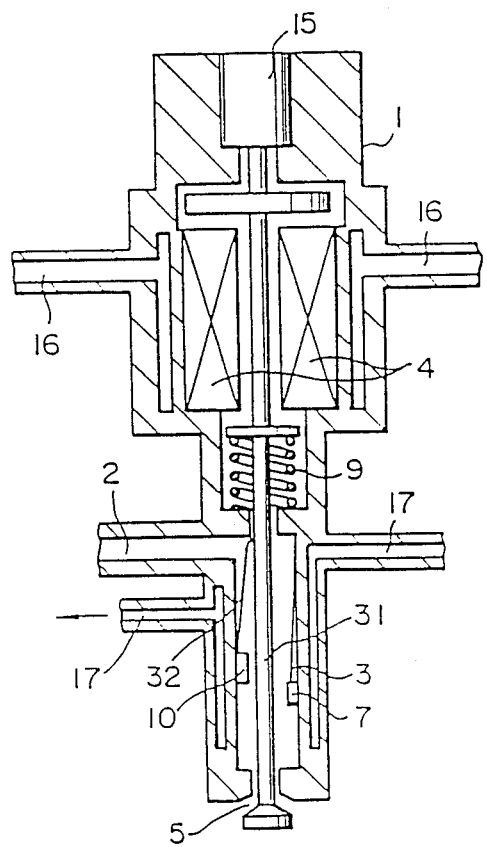
FIG. 19 is a cross-sectional view of a gas sampling valve having sensors mounted near the gas sampling inlet.

In the above-described embodiments, the λ sensors and the catalyst are mounted on the gas flow passage. However, the sensor attachment portion 6 may be disposed inside the gas sampling valve housing in order to further improve the response and reduce the necessary amount of sampled gas. FIG. 19 shows an example in which small λ sensors 7 and 10 are mounted on the side of the gas sampling inlet 5 of the housing 1. In FIG. 19, portions including components corresponding to those shown in FIG. 14 are indicated by the same reference characters and a description of them is therefore omitted.

In the embodiment shown in FIG. 18, the flow passage diverges into the branch portions communicated with the gas analyzer and the sensor attachment portion. However, this divergence is not necessary in a case where the sensor is so small that there is no possibility of the composition of sampled gas being greatly changed by the catalytic activity on the surface of the electrode of the sensor and that analysis of gas downstream of the sensor attachment portion 6 has no influence on the results of gas analysis.

Figure 20:
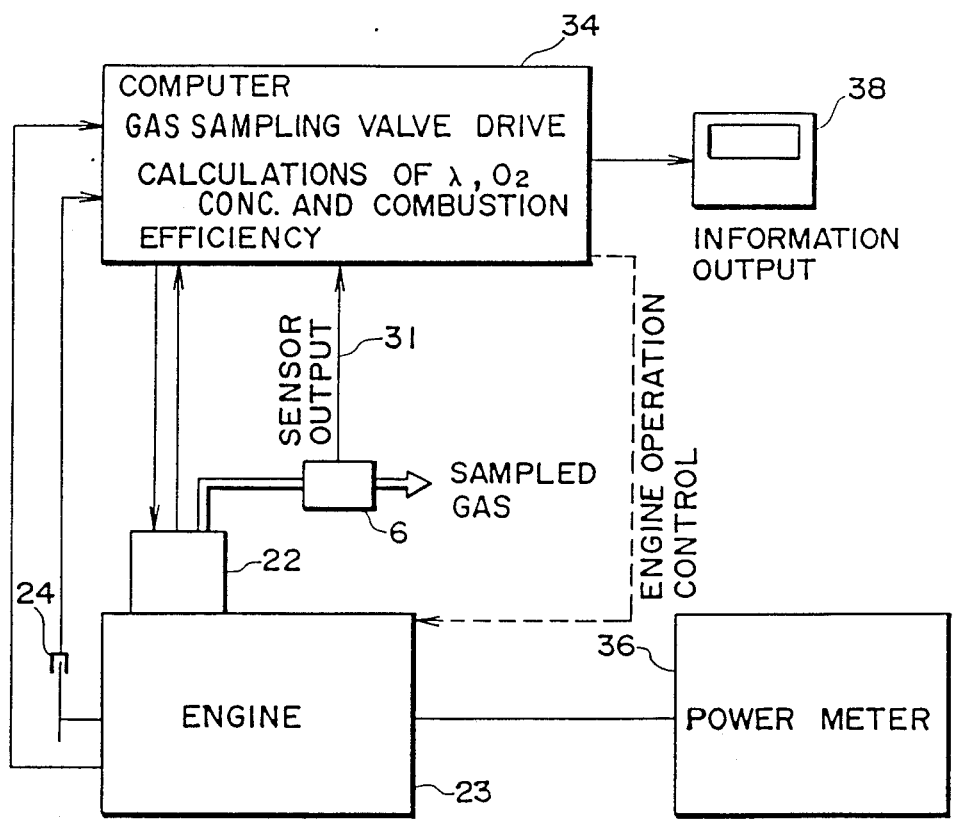
FIG. 20 is a block diagram of an engine test system which makes use of a gas sampling valve in accordance with the above embodiments.

FIG. 20 shows a gas sampling test system in which the gas sampling valve described above as one of the embodiments is used. In this system, a computer 34 simultaneously performs calculation of control of the gas sampling valve, lift monitor, λ and oxygen concentration, and combustion efficiency, the results of calculation being output to a CRT 38.

The use of the above-described gas sampling valve is not limited to application to tests of engines, and the gas sampling valve in accordance with the present invention can be used as a detector for various types of combustion systems. The gas sampling valve in accordance with the present invention may be of a mechanical type (cam drive) as well as an electromagnetic type. The gas sampling test system is not limited to the test system shown in FIG. 20. Such a system can be mounted on a vehicle and used to control the engine.

What is claimed is:

1. A gas sampling valve, comprising:
    a housing having a small opening for gas sampling, provided in a combustion chamber, and a gas flow passage one end of which communicates with the outside and the other end of which communicates with said small opening;
    a valve for opening and closing said small opening;
    an operating mechanism for operating said valve in synchronization with the rotation of an engine and for introducing a local gas near said small opening into said gas flow passage; and
    at least one detector for detecting the concentration of components of sampled gas, disposed in said gas flow passage a predetermined distance from said small opening.

2. A gas sampling valve according to claim 1, wherein said detector comprises a lean λ sensor.

3. A gas sampling valve according to claim 2, further comprising a catalyst disposed in said gas flow passage between said small opening and said lean λ sensor.

4. A gas sampling valve according to claim 3, wherein said detector comprises:
    a first lean λ sensor for detecting a concentration of oxygen before catalytic combustion, and
    a second lean λ sensor for detecting a concentration of oxygen after catalytic combustion.

5. A gas sampling valve according to claim 4, wherein said first lean λ sensor is disposed between said small opening and said catalyst and said second lean λ sensor is disposed downstream of said catalyst, and further comprising means for calculating combustion efficiency from detected concentrations of oxygen.

6. A gas sampling valve according to claim 1, wherein said detector comprises a lean λ sensor which exhibits catalytic activity.

7. A gas sampling valve according to claim 1, wherein said detector comprises a wide-range air fuel ratio sensor.

8. A gas sampling valve according to claim 7, further comprising a catalyst disposed in said gas flow passage between said small opening and said wide-range air fuel ratio sensor.

9. A gas sampling valve according to claim 8, wherein said detector further comprises a second wide-range air fuel ratio sensor disposed between said small opening and said catalyst.

10. A gas sampling valve according to claim 1, wherein said detector comprises a wide-range air fuel ratio sensor which exhibits catalytic activity.

11. A gas sampling valve according to claim 1, wherein said at least one detector comprises two lean λ sensors, one of which exhibits catalytic activity, and said two lean λ sensors being disposed in said gas flow passage in any order.

12. A gas sampling valve according to claim 11, wherein said two lean λ sensors comprise:

a first lean λ sensor with substantially no catalytic activity for detecting concentration of oxygen before catalytic combustion, and a second lean λ sensor with catalytic activity for detecting concentration of oxygen after catalytic combustion, and further comprising means for calculating combustion efficiency from detected concentrations of oxygen.

13. A gas sampling valve according to claim 1, wherein said at least one detector comprises two wide-range air fuel ratio sensors, one of which exhibits catalytic activity, and said two wide-range air fuel ratio sensors being disposed in said gas flow passage in any order.

14. A gas samplying valve according to claim 1, wherein said detector comprises an oxide solid electrolyte pinched between a cathode and an anode, and a cover with at least one small opening or a porous layer disposed on or over said cathode, said cathode and said anode being connected to a power source.

* * * * *